United States Patent [19]

Witte et al.

[11] 3,997,666
[45] Dec. 14, 1976

[54] 1-[3-(NAPHTH-1-YLOXY)-2-HYDROXY-PROPYL]-PIPERAZINE COMPOUNDS AND THERAPEUTIC COMPOSITIONS

[75] Inventors: Ernst-Christian Witte, Mannheim; Kurt Stach, Mannheim-Waldhof; Max Thiel, Mannheim; Gisbert Sponer, Hemsbach; Egon Roesch, Mannheim, all of Germany

[73] Assignee: Boehringer Mannheim G.m.b.H., Mannheim, Germany

[22] Filed: Jan. 28, 1975

[21] Appl. No.: 544,719

[30] Foreign Application Priority Data

Feb. 23, 1974 Germany .......................... 2408804

[52] U.S. Cl. .................... 424/250; 260/268 BC
[51] Int. Cl.² .................................. C07D 295/08
[58] Field of Search ............. 260/268 PH, 268 BC; 424/250

[56] References Cited

UNITED STATES PATENTS

| | | | |
|---|---|---|---|
| 3,701,777 | 10/1972 | Edenhofer et al. | 260/268 PH |
| 3,856,794 | 12/1974 | Danilewicz et al. | 260/268 PH |
| 3,947,446 | 3/1976 | Witte et al. | 260/268 BC |

OTHER PUBLICATIONS

Cronenberger et al., Chemical Abstracts, vol. 66, 85761j (1967).
Pollard et al., J. Org. Chem., vol. 23 (1958) pp. 1935–1937.

*Primary Examiner*—Paul M. Coughlan, Jr.
*Attorney, Agent, or Firm*—Burgess, Dinklage & Sprung

[57] ABSTRACT

New 1-[3-(naphth-1-yloxy)-2-hydroxypropyl]-piperazine compounds of the formula:

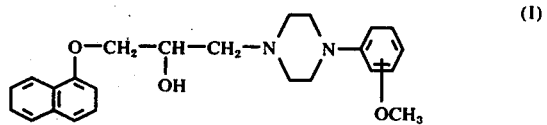

(I)

and the pharmacologically compatible salts thereof are outstandingly effective in lowering blood pressure and are thus useful as anti-hypertensive agents.

5 Claims, No Drawings

1-[3-(NAPHTH-1-YLOXY)-2-HYDROXYPROPYL]-PIPERAZINE COMPOUNDS AND THERAPEUTIC COMPOSITIONS

The present invention relates to 1-[3-(naphty-1-yloxy)-2-hydroxypropyl]-piperazine compounds and to therapeutic compositions and uses thereof.

The new 1-[3-(naphth-1-yloxy)-2-hydroxypropyl]-piperazine derivatives according to the present invention are compounds of the general formula:

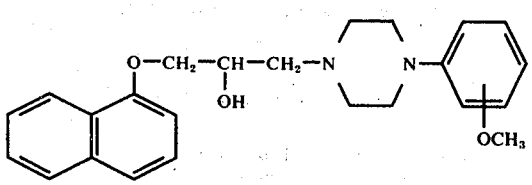

(I)

and the pharmacologically compatible salts thereof.

The new compounds according to the present invention possess outstanding blood pressure-lowering and thus anti-hypertensive properties. Furthermore, in the case of rats, they inhibit the anaphylactoid reactions initiated by dextran.

In J. Org. Chem., 23, 1935/1958, some 1-[3-(naphth-1-yloxy)-2-hydroxypropyl]-piperazines are described but there is no mention of their pharmacological action. As our investigations have shown, the new compounds (I) according to the present invention possess, surprisingly, a substantially better anti-hypertensive action than the previously described compounds.

The new compounds according to the present invention can be prepared, for example, by one of the following methods:

a. reaction of a compound of the general formula:

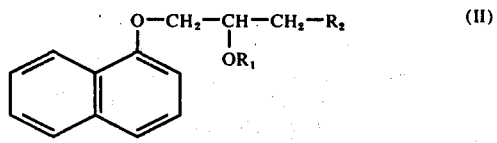

(II)

wherein $R_1$ is a hydrogen atom and $R_2$ is a halogen atom or wherein $R_1$ and $R_2$ together represent a valency bond, with a methoxyphenyl-piperazine of the general formula:

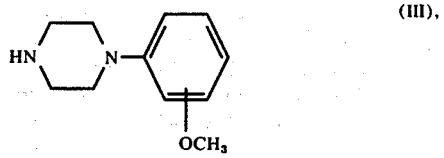

(III), or b. reaction of 1-naphthol with a compound of the general formula:

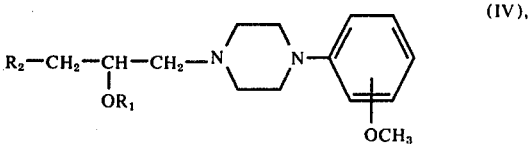

(IV), wherein $R_1$ and $R_2$ have the same meanings as above; whereafter, if desired, the compounds obtained are converted into their pharmacologically compatible salts.

When $R_2$ represents a halogen atom, it is preferably a chlorine atom.

The reaction can be carried out by mixing molar amounts of the reaction components and leaving the mixture to stand at ambient temperature; the reaction can be accelerated by brief heating, possibly in a pressure vessel. If desired, a solvent, for example a lower alcohol, can also be added to the reaction mixture.

For the preparation of the salts, the compounds according to the present invention are reacted with pharmacologically compatible inorganic or organic acids, for example, hydrochloric acid, sulfuric acid, phosphoric acid, lactic acid, citric acid or an alkyl-sulfonic acid.

The following Examples are given for the purpose of illustrating without limiting, the present invention:

EXAMPLE 1

Preparation of 1-(2-Methoxyphenyl)-4-[3-(naphth-1-yloxy)-2-hydroxypropyl]-piperazine A mixture of 30.0 g. (0.15 mol) 2,3-epoxy-1-(1-naphthyloxy)-propane and 28.8 g. (0.15 mol) 1-(2-methoxy-phenyl)-piperazine was heated to 120° C. and maintained at this temperature for 5 hours. After cooling, a red solidified product was obtained which was recrystallized from isopropanol and had a melting point of 125° – 126° C. There were obtained 46.5 g. (79% of theory) 1-(2-methoxy-phenyl)-4[3-(naphth-1-yloxy)-2-hydroxypropyl]-piperazine. The corresponding dihydrochloride, after recrystallization from methanol/ethanol (1:2), had a melting point of 212° – 213° C.

EXAMPLE 2

Preparation of 1-(4-Methoxyphenyl)-4-[3-(naphth-1-yloxy)-2-hydroxypropyl]-piperazine 20.0 g. (0.1 mol) 2,3-epoxy-1-(1-naphthyloxy)-propane were mixed with 30 ml. ethanol and 19.2 g. (0.1 mol) 1-(4-methoxyphenyl)-piperazine, whereafter the reaction mixture was heated to 60° C. and maintained at this temperature for 6 hours. The reaction mixture was then left to stand overnight and the ethanol subsequently evaporated off. The oily residue was dissolved in chloroform, hydrogen chloride was passed through the chloroform solution and then ether was added, the dihydrochloride thereby precipitating out. This was filtered off with suction and recrystallized from methanol/ethanol (1:3). There was obtained 1-(4-methoxy-phenyl)-4-[3-(naphth-1-yloxy)-2-hydroxypropyl]-piperazine in a yield of 76% of theory. The product had a melting point of 237° – 238° C.

The compounds of the invention constitute potent antihypertensive agents. The compounds have proved particularly effective in the treatment of patients with severe or sustained elevation of blood pressure, particularly diastolic pressure. The compounds are suitable for use in almost all forms of fixed and progressive hypertensive disease, including that in which blood pressure is moderately elevated. The compounds have also proved effective in renal hypertension, including hypertension secondary to pyelonephritis, glomerulonephritis and renal amyloidosis.

The compounds can be administered orally, as pills, tablets, capsules, powders and the like. The preferred form of oral administration is as a tablet contaning 1 to 20 mg of active compound.

The compounds can also be administered parenterally. Injection solutions containing 10 mg/ml of injection solution are preferred.

The dosage schedule is entirely dependent on the condition of the patient, his response to the treatment and whether or not he is ambulatory or hospitalized. The treatment should be begun with small doses (1 mg) and increased gradually depending upon the patient's response. The dosage can be increased at 5 to 7 day intervals until an average daily dose of 1 to 20 mg is reached. Only one dose a day is usually required.

In order to establish the effectiveness of the new compounds of the invention as agents for reducing blood pressure, a series of tests as follows were carried out.

The following were the test methods used:

The test animals were beagles of both sexes into which polyethylene catheters had been implanted in the arteria and vena femoralis. The operation was effected under sterile conditions and under pentobarbital [5-ethyl-5-(1-methylbutyl)barbituric acid]. Meticulous care of the animals and prophylactic administration of antibiotics avoided post-operative complications, so that after a few days the animals were available for the experiments in clinically healthy condition and with the correct physiological characteristics.

During the course of the tests the blood pressure of the dogs was measured via the arterial catheter as well as by an electromechanical pressure transformer (Bell & Howell, 4/327/L 221) and continuously registered on a cable code direct printer (Company Schwarzer, Physiograph). The animals were lying on a table during the tests and were not influenced by any drugs other than the test preparations.

Before the application of the test substance, blood pressure was determined for at least 30 minutes. Then the test compounds were injected via the venous catheter within a time period of one minute in a volume of 0.2 ml/kg at a dosage of test compound of 2.5 mg/kg of body weight. The change in the blood pressure 60 minutes after administration of the test substance, relative to the initial value, was measured as a criterion of effectiveness.

Each substance was tested on 4 to 6 dogs and the blood pressure depression values set forth in the Table below represent mean values of the individual tests.

TABLE

Influence on blood pressure (in mm Hg) by intravenous injection of 2.5 mg/kg of various phenylpiperazines (Change in the initial values 60 minutes after injection of the test compound.)

| TEST COMPOUND | $\Delta \bar{p}$ |
|---|---|
| Comparison Compounds: | |
| 1-Phenyl-4-[3-(naphth-1-yl-oxy)-2-hydroxy-propyl]-piperazine* | − 1 |
| 1-(4-Chlorophenyl)-4-[3-(naphth-1-yl-oxy)-2-hydroxy-propyl]-piperazine (described in J. Org. Chem. 23 (1958) p. 1935) | + 2 |
| Inventive Compounds: | |
| 1-(2-Methoxyphenyl)-4-[3-(naphth-1-yl-oxy)-2-hydroxy-propyl]-piperazine | −19 |
| 1-(4-Methoxyphenyl)-4-[3-(naphth-1-yl-oxy)-2-hydroxy-propyl]-piperazine | − 3 |

*After the application of this substance incompatibility symptoms appeared in form of dyspnea, restlessness and repeated vomiting.

The data in the above table show that the inventive compounds were markedly superior to the comparison substances in lowering blood pressure, i.e., were from 3 to 19 times as effective as the better of the comparison materials, and it must further be noted that the better comparison material induced the undesirable side effects noted above.

The present invention also provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative but not limitative of the present invention and that other embodiments within the spirit and scope of the invention will suggest themselves to those skilled in the art.

What is claimed is:
1. 1-(2-Methoxyphenyl)-4-[3-(naphth-1-yloxy)-2-hydroxypropyl]-piperazine.
2. 1-(2-Methoxyphenyl)-4-[3-naphth-1-yloxy)-2 hydroxypropyl]-piperazine in its pharmacologically compatible salt form.
3. Therapeutic composition for combating hypertension comprising a pharmaceutically acceptable carrier and as an active ingredient 1-(2-methoxyphenyl)-4-[3-(naphth-1-yloxy)-2-hydroxypropyl]-piperazine.
4. Method of combating hypertension in a subject which method comprises administering to such subject effective amounts of 1-(2-methoxyphenyl)-4-[3-(naphth-1-yloxy)-hydroxypropyl]-piperazine.
5. Method as claimed in claim 4, wherein said compound is applied at a dosage of 1 to 20 mg per 75 kg of body weight of the subject.

* * * * *